United States Patent [19]
Rego, Jr. et al.

[11] Patent Number: 5,364,400
[45] Date of Patent: Nov. 15, 1994

[54] INTERFERENCE IMPLANT

[75] Inventors: Richard P. Rego, Jr., Mansfield; Bernard J. Bourque, Taunton, both of Mass.

[73] Assignee: American Cyanamid Co., Wayne, N.J.

[21] Appl. No.: 81,596

[22] Filed: Jun. 23, 1993

Related U.S. Application Data

[63] Continuation-in-part of Ser. No. 836,674, Feb. 14, 1992.

[51] Int. Cl.$^5$ ............................................. A61B 17/56
[52] U.S. Cl. ........................................ 606/72; 606/73; 606/77
[58] Field of Search .................. 606/72–77, 606/104; 81/461, 448, 449, 452; 411/394, 995, 407, 408

[56] References Cited

U.S. PATENT DOCUMENTS

| | | | |
|---|---|---|---|
| 2,814,296 | 11/1957 | Everett | 128/339 |
| 3,103,926 | 9/1963 | Cochran | 606/73 |
| 3,494,243 | 2/1970 | Kleinhenn | 85/1 |
| 3,584,667 | 6/1971 | Reiland | 145/50 |
| 3,739,773 | 6/1973 | Schmitt et al. | 606/62 |
| 3,977,081 | 8/1976 | Zambelli et al. | 32/10 |
| 4,012,551 | 3/1977 | Bogaty et al. | 428/192 |
| 4,145,764 | 3/1979 | Suzuki et al. | 606/76 |
| 4,275,813 | 6/1981 | Noiles | 206/339 |
| 4,362,162 | 12/1982 | Nakajima et al. | 128/334 |
| 4,429,080 | 1/1984 | Casey et al. | 606/219 |
| 4,454,612 | 6/1984 | McDaniel et al. | 606/76 |
| 4,632,100 | 12/1986 | Somers | 606/73 |
| 4,655,222 | 4/1987 | Florez et al. | 128/334 |
| 4,711,234 | 12/1987 | Vives et al. | 606/76 |
| 4,788,979 | 12/1988 | Jarrett et al. | 128/335.5 |
| 4,835,819 | 6/1989 | Duffy et al. | 427/195 |
| 4,898,186 | 2/1990 | Ikada et al. | 606/77 |
| 4,927,421 | 5/1990 | Goble et al. | 606/73 |
| 4,944,742 | 7/1990 | Clemow et al. | 606/77 |
| 4,950,270 | 8/1990 | Bowman et al. | 606/72 |
| 4,976,715 | 12/1990 | Bays et al. | 606/77 |
| 5,053,036 | 10/1991 | Perren et al. | 606/77 |
| 5,062,843 | 11/1991 | Mahony | 606/76 |
| 5,108,399 | 4/1992 | Eitenmuller et al. | 606/76 |
| 5,129,906 | 7/1992 | Ross | 606/77 |
| 5,139,499 | 8/1992 | Small | 606/73 |
| 5,156,616 | 10/1992 | Meadows | 606/73 |

FOREIGN PATENT DOCUMENTS

| | | |
|---|---|---|
| 0276153A2 | 7/1988 | European Pat. Off. . |
| 0317406 | 5/1989 | European Pat. Off. . |
| 0409364 | 1/1991 | European Pat. Off. . |
| 0451932A1 | 10/1991 | European Pat. Off. . |
| 0469441A1 | 2/1992 | European Pat. Off. . |
| 0502698 | 9/1992 | European Pat. Off. . |
| 3811345 | 7/1989 | Germany . |
| 86/03666 | 7/1986 | WIPO . |
| 89/01767 | 3/1989 | WIPO . |
| 89/09030 | 10/1989 | WIPO . |
| 90/08510 | 8/1990 | WIPO . |

OTHER PUBLICATIONS

Brochure "Biofix-Screw", Bioscience Ltd. (Undated).
Leslie S. Matthews, M.D. & Stephen R. Soffer, M.D., Pitfalls in the Use of Interference Screws for Anterior Cruciate Ligament Reconstruction: Brief Report, Published Arthroscopy, 1989.
Kurosaka et al., A Biomechanical Comparison of Different Surgical Techniques of Graft Fixation in Anterior Cruciate Ligament Reconstruction, Am. J. Sports Medicine 15:225-9 (1987).
Brochure "When It Comes To ACL, Why Screw Around With Anyone Else?", Published 1990.

*Primary Examiner*—Michael A. Brown
*Attorney, Agent, or Firm*—Douglas E. Denninger

[57] ABSTRACT

A surgical interference implant including an elongated body formed of a biocompatible material and having a distal end and a proximal end. The proximal end defines an element for engaging a driver, and lacks an enlarged head member. The body defines a conical region having a smooth outer surface which extends proximally along a first, distal portion of the body to enable initial linear insertion of the body into a bone tunnel. A helical thread is disposed about a second, proximal portion of the body to enable subsequent rotational insertion of the body deeper into the bone tunnel.

19 Claims, 5 Drawing Sheets

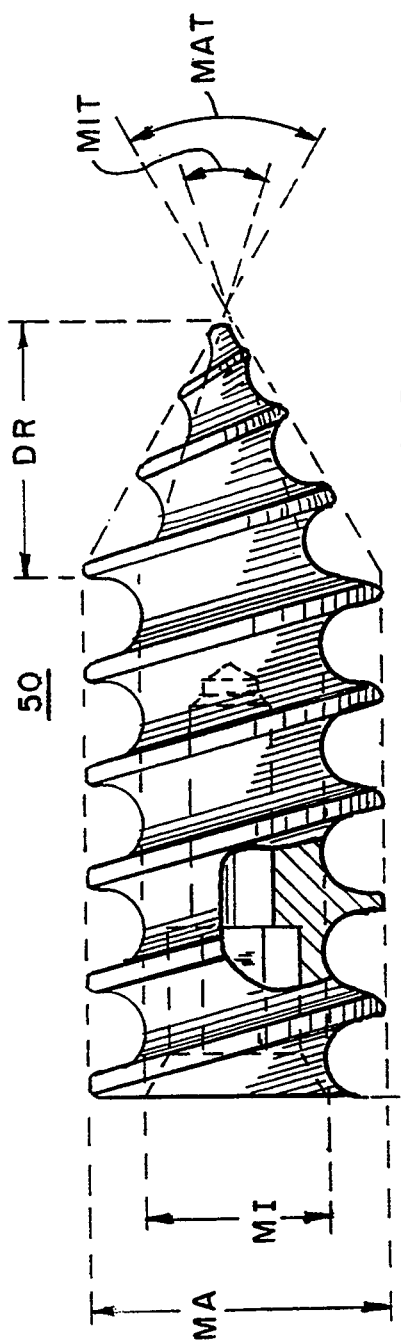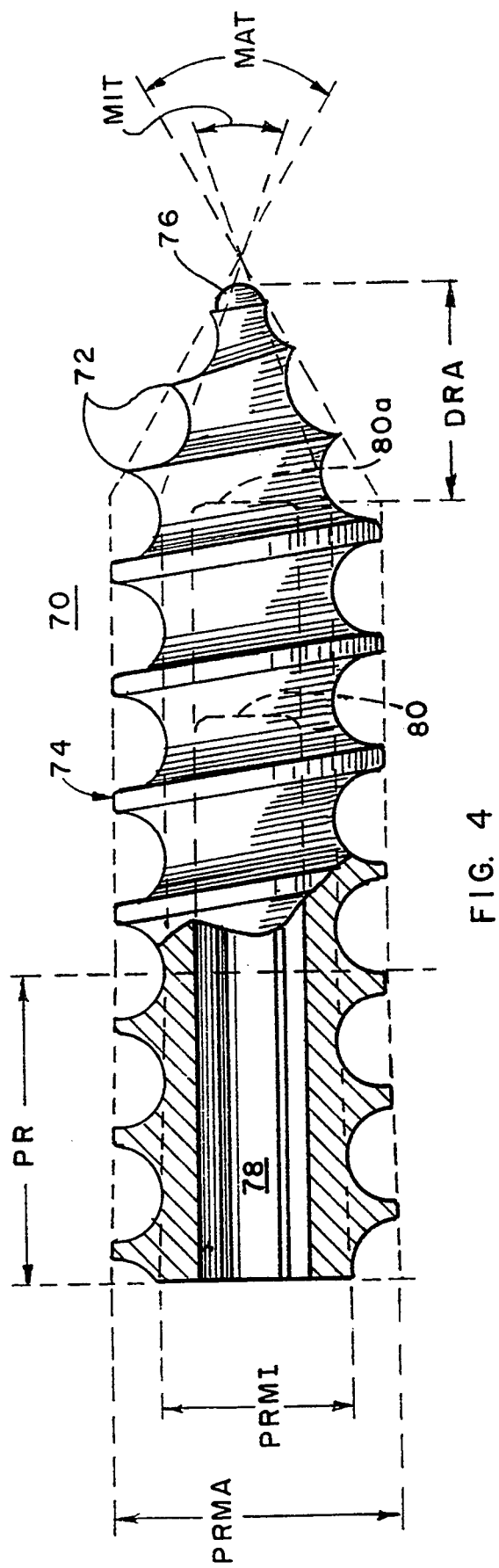

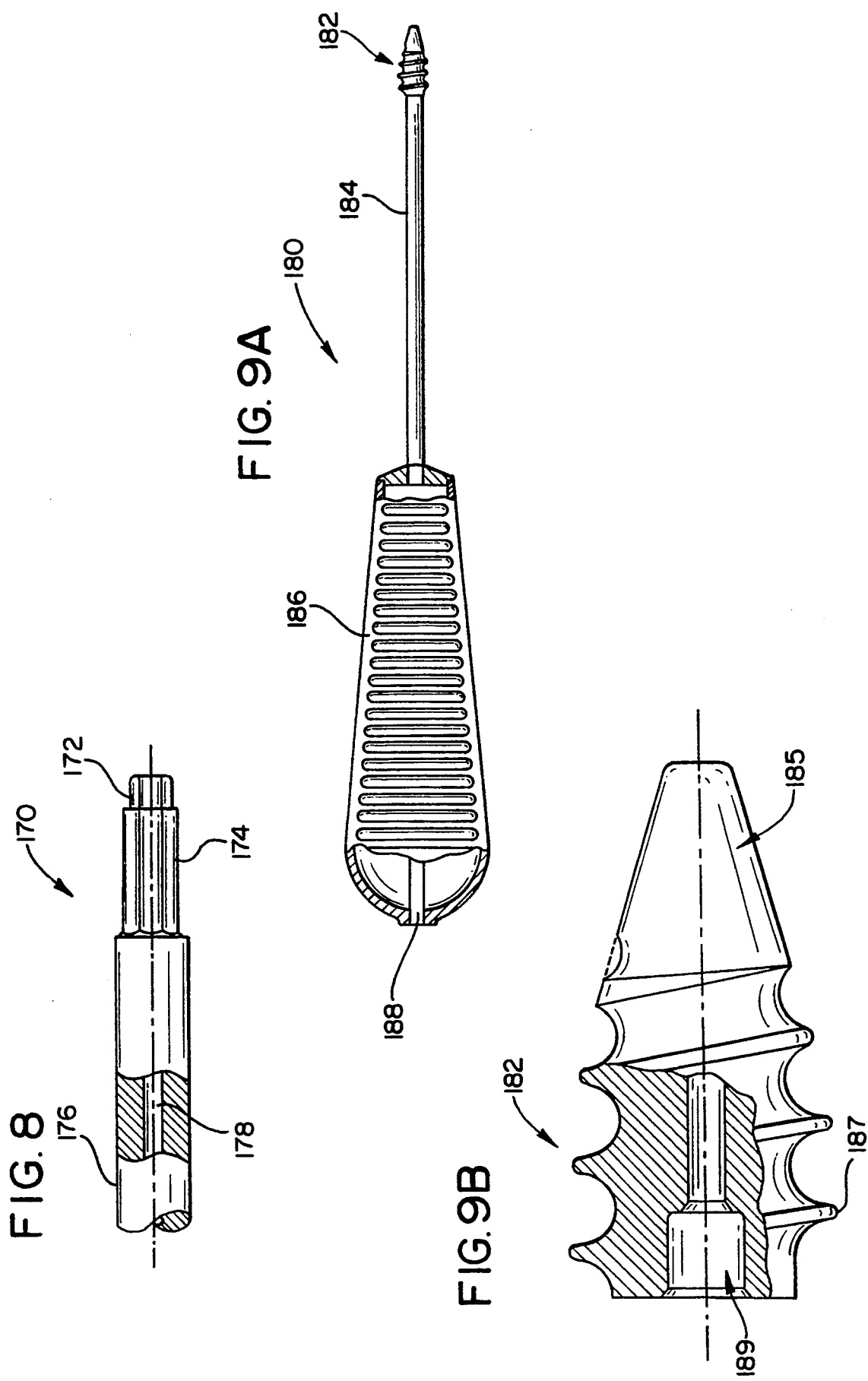

INTERFERENCE IMPLANT

RELATED INVENTION

This application is a continuation-in-part of U.S. Ser. No. 07/836,674 (Small, et al.) filed Feb. 14, 1992, which is incorporated herein by reference.

FIELD OF THE INVENTION

This invention relates to surgical interference screws, and more particularly to improved implants capable of more rigid and direct insertion with minimal stress being placed on the implant.

BACKGROUND OF THE INVENTION

There are a number of surgical procedures in which a fastener such as a screw or nail is inserted into a tissue of a patient. One surgical use involves insertion of an interference screw into a bone tunnel or channel to secure a bone plug in place and thereby attach an end of an anterior cruciate ligament (ACL) replacement. ACL reconstruction procedures and interference screws are disclosed for example in U.S. Pat. Nos. 5,139,499 and 5,139,520, both incorporated herein by reference.

Surgeons and patients desire absorbable implants which will be partially or completely absorbed by the body. An absorbable lag screw for fracture fixation and having an enlarged, rounded head, for example, is disclosed in German Patent DE 3,811,345.

A relatively large amount of torque must be applied to an interference screw during insertion. A screw formed from a bioabsorbable material is likely to have a significantly lower strength, however, and therefore should not be subjected to high torque during insertion. The distal region of a bioabsorbable screw is particularly susceptible to shear failure due to excess torque. It would be desirable to improve the configuration of the screw or to lower the amount of torque which must be applied to the screw.

Another type of interference device has annular ribs or ridges and is linearly inserted into a hole drilled in a bone. As disclosed in European Patent No. 317,406, for example, a conical peg having a plurality of annular ridges is driven linearly into a bone tunnel between the tunnel wall and a replacement ligament.

It is generally more difficult to precisely control the depth of insertion of such a linearly inserted implant and to control the amount of frictional engagement between the implant and the bone. Further, the tunnel walls are scraped or shaved to some extent by the annular ridges which may generate undesirable debris and expand the tunnel to the greatest outer diameter of the implant. Additionally, a bone plug within the bone tunnel might be unintentionally driven deeper into the tunnel.

SUMMARY OF THE INVENTION

Therefore, it is an object of the present invention to provide an improved interference implant which eliminates initial insertion torque yet provides controllable insertion for final placement.

It is a further object of this invention to provide such an implant for which insertion torque commences gradually and is lowest at the distal region to minimize shear failure due to torsion.

Yet another object of this invention is to provide such an implant having a configuration which enhances use of bioabsorbable materials.

A still further object of this invention is to provide an improved implant which minimizes unintended driving of a bone plug deeper into a bone tunnel, and does not expand bone tunnel to the greatest overall diameter of the implant.

This invention features a surgical interference implant including an elongated body formed of a biocompatible material and having a distal end and a proximal end. The proximal end defines an element for engaging a driver, and lacks an enlarged head member. The body defines a conical region having a smooth outer surface which extends proximally along a first, distal portion of the body to enable initial linear insertion of the body into a bone tunnel. A helical thread is disposed about a second, proximal portion of the body to enable subsequent rotational insertion of the body deeper into the bone tunnel.

In one embodiment, the helical thread extends from a proximal edge of the smooth outer surface to the proximal end of the body. The first, distal portion is inclined at a first angle relative to a longitudinal axis of the elongated body, and one of a body major diameter and a body minor diameter of the second, proximal portion is inclined at a second, more acute angle. The body major diameter is the outer diameter of the threads, while the minor diameter is the root or bottom portion of the threads.

In one of the preferred embodiments, the elongated body defines a passageway extending between the distal and proximal ends to accommodate a guide wire, and the body is formed of a bioabsorbable material. The element for engaging a driver includes a polygonal drive socket formed in the proximal end of the body.

This invention also features a method of securing an object within a bone tunnel, including forming a tunnel in the bone, inserting an object into the bone tunnel, and providing an interference implant as described above. An appropriately-sized driver is selected and connected with the driver engaging element of the interference implant. The interference implant is linearly inserted partially into the bone tunnel between the object and the wall of the tunnel until a portion of the helical thread lies within the tunnel. Subsequently, torque is applied to the driver to rotate the interference implant spirally about its longitudinal axis which causes the implant to screw deeper into the bone tunnel to secure the object within the tunnel. This method is particularly suited for securing a bone plug of a replacement ligament into a femur at a knee joint.

BRIEF DESCRIPTION OF THE DRAWINGS

Other objects, features and advantages will occur from the following description of preferred embodiments and the accompanying drawings, in which:

FIG. 3 is a side view of a conventional metal 7 mm interference screw;

FIG. 4 is a side view of a novel 7 mm absorbable interference screw;

FIG. 8 is a side, partial cross-sectional view of the distal end of a driver for use with the interference implant of FIG. 7;

FIG. 9A is a schematic side, partial cross-sectional view of a cannulated tap which may be used to prepare a path for the interference implant; and FIG. 9B is an enlarged, side, partial cross-sectional view of the distal end of the tap of FIG. 9A.

DETAILED DESCRIPTION OF THE PREFERRED EMBODIMENTS

Figure 6:
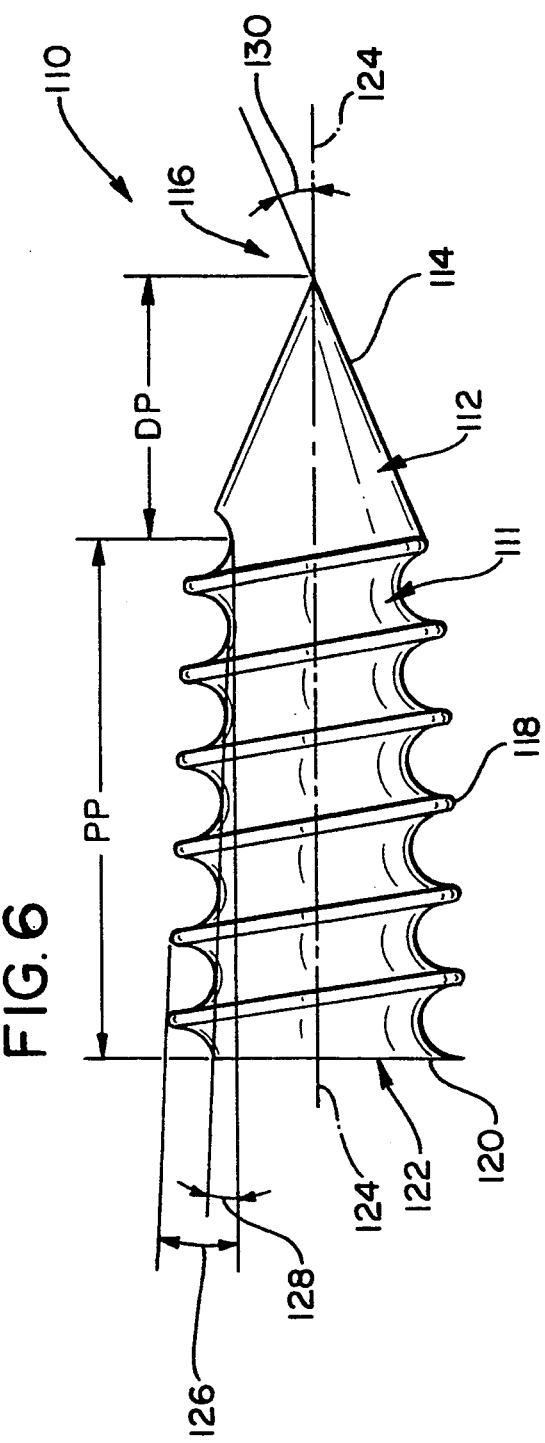
FIG. 6 is a side view of an improved interference implant according to the present invention.
Figure 7:
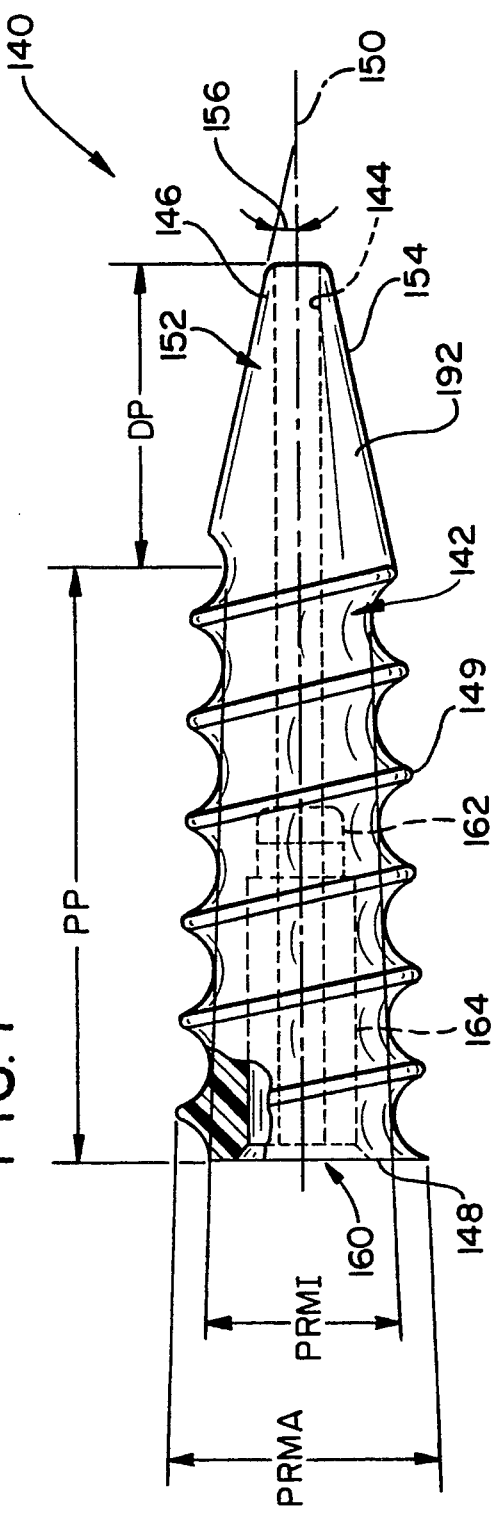
FIG. 7 is a side, partial cross-sectional view of a cannulated interference implant according to the present invention.

This invention may be accomplished by an improved interference implant which enables initial linear insertion into a bone channel by pushing or hammering, thereby eliminating initial insertion torques, and has a helical thread disposed over the remainder of the implant to enable subsequent rotational insertion of the implant deeper into the bone tunnel. Subsequent insertional torque commences gradually and is lowest at the distal region, which is otherwise most susceptible to shear failure due to excess torsion. Two such interference implants 110 and 140 are shown in FIGS. 6–7 and are discussed in more detail below.

Figure 1:
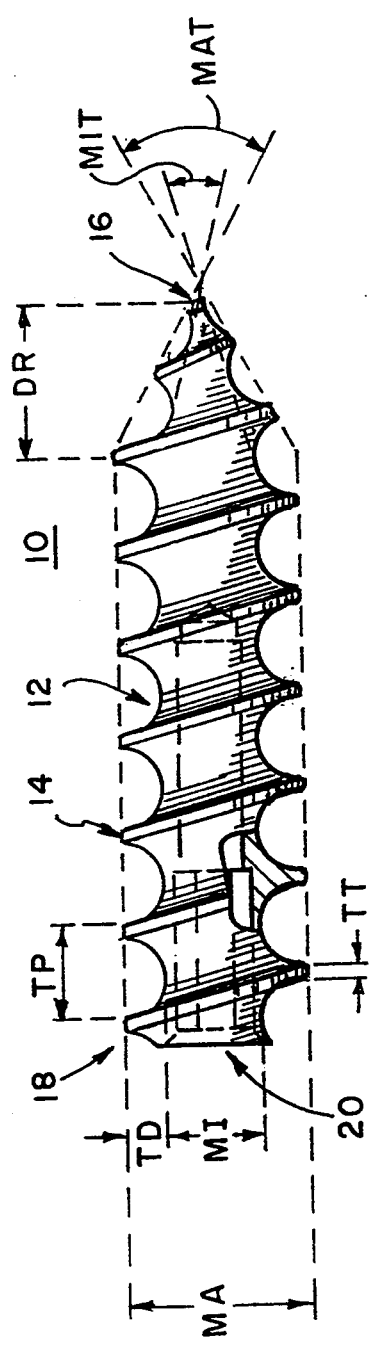
FIG. 1 is a side view of a conventional metal 5.5 mm interference screw.

Cannulated and non-cannulated titanium alloy interference screws having a major diameter of 5.5 mm for screw 10, FIG. 1, and major diameters of 7.0 mm and 9.0 mm for screw 50, FIG. 3, are commercially available in lengths of 20 mm to 30 mm from Acufex Microsurgical, Inc., Mansfield, Mass. Non-cannulated versions are illustrated in FIGS. 1 and 3.

Conventional interference screw 10, FIG. 1, includes an elongated body 12 formed of a titanium alloy which defines a helical thread 14 about its exterior surface extending from distal end 16 to proximal end 18. A hexagonal drive socket 20 is defined at the proximal end 18.

Several dimensions applicable to all screws described herein are indicated as thread pitch TP, thread thickness TT, thread depth TD, major diameter MA, and minor diameter MI. Each screw further defines a distal region DR, although the thread thickness in this region is substantially less for the novel polymeric interference screws shown in FIGS. 2, 4, and 5. Over the proximal remainder of the polymeric screw's helical thread, however, the thread thickness is greater than that of conventional metal screws. For all screws illustrated in FIGS. 1–5, the helical thread in the distal region DR has a major diameter taper angle of MAT and minor diameter angle taper of MIT; the distal region for polymeric screws is referred to as region DRA.

In general, interference implants according to the present invention preferably are formed of a bioabsorbable material and have an increased thread thickness TT and a decreased thread depth TD to increase overall rigidity and strength of the absorbable interference screw. This improved construction enables use of bioabsorbable materials which are more brittle and have less strength than metal materials.

Figure 2:
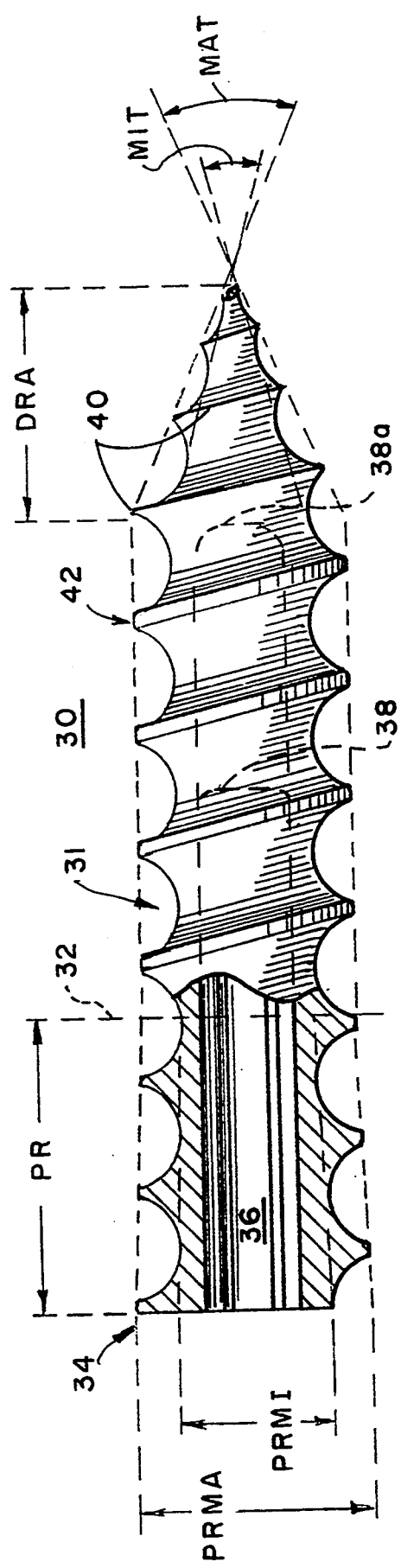
FIG. 2 is a side view of a novel 5.5 mm absorbable interference screw.

Novel absorbable interference screw 30, FIG. 2, has the same major diameter MA of screw 10 up to boundary 32. From boundary 32 to proximal end 34, the elongated body 31 exhibits an increase in major diameter up to a maximum proximal region major diameter of PRMA. Also, there is an increase in minor diameter in proximal region PR up to maximum proximal region minor diameter PRMI.

The absorbable screw 30 defines a drive socket 36 at its proximal end which extends at least half-way along the length of the elongated body 31 to terminate distally in a socket base 38. In another construction, the socket base continues further to socket base 38a. The drive socket 36 is polygonal when viewed from proximal end 34, preferably in the shape disclosed in U.S. Pat. No. 3,584,667 (Reiland).

The crests 40 of helical thread 42 within distal region DRA have a shallower thread and culminate in a peak or edge rather than in a thickened crest as found in the proximal remainder of the thread 42. As described in more detail below, the distal region of interference implants according to the present invention is smooth and unthreaded.

Absorbable screws 70, FIG. 4, includes helical crests 72 of helical thread 74 within distal region DRA culminating in an edge, and the distal tip 76 is rounded. Drive socket 78 terminates distally in a socket base 80 or 80a.

Polymeric interference screw 90, FIG. 5, has its exterior surface covered with a coating 92 as described in more detail below.

Thread crests 94 of helical thread 96 within distal region DRA have a relatively sharp edge and elongated screw body 97 terminates in a rounded distal tip 98. Polygonal drive socket 100 terminates distally in a socket base 102 or 102a.

Interference implant 110, FIG. 6, according to the present invention has a conical region 112 with a smooth outer surface 114 which extends proximally from distal end 116 along a first, distal portion DP. A helical thread 118 is disposed about a second, proximal portion PP which extends proximally up to and including proximal end 120. A drive socket 122 is centered within proximal end 120 along longitudinal axis 124.

In one construction, the helical threads 118 have a thread pitch of 0.110 inch and a thread thickness of 0.013 inch. The elongated body 111 has a body major diameter taper at angle 126 of between one degree to ten degrees, preferably two to three degrees. Similarly, the body minor or root diameter increases at angle 128 of preferably two to three degrees. By comparison, the conical region 112 tapers at an angle 130 of between ten to twenty-five degrees, which is less acute than angles 126 or 128.

The term conical is used to denote a shape of a solid generated by rotating a right triangle about one of its legs. A subset of this shape is frustoconical, in which the cone has a blunt tip.

Cannulated interference implant 140, FIG. 7, according to the present invention includes an elongated body 142 which defines a central passage 144 which extends from distal end 146 to proximal end 148 along longitudinal axis 150. A conventional guide wire is insertable through the passage 144 as described in more detail below.

The interference implant 140 defines a frustoconical region 152 in distal portion DP. The smooth outer surface 152 is tapered at an angle 156 of thirteen degrees in one construction. Helical thread 149 extends along the entire length of proximal portion PP. The passageway 144 has a diameter of 0.065 inch to accommodate a conventional guidewire having a diameter of 0.062 inch.

In one construction, the elongated body 142 has an overall length of 0.803 inch, a length of proximal portion PP of 0.466 inch, and a length of distal portion DP of 0.337 inch. In another construction, the body 142 has an overall length of 1.197 inch, proximal portion PP has a length of 0.860 inch, and distal portion DP again has a length of 0.337 inch. In the first-described construction, the body 142 has a maximum proximal region major diameter PRMA of 0.278 inch and a maximum proximal region minor of PRMI of 0.200 inch; in the second-described construction, PRMA equals 0.306 inch and PRMI equals 0.228 inch. A drive socket 160 is formed in the proximal end 148 having an inner hexagonal section 162 and a second drive section 164 which preferably shape disclosed in U.S. Pat. No. 3,584,667 (Reiland).

The distal portion of a driver 170 is shown in FIG. 8 with a first, hexagonal projection 172 and a second drive section 174 as disclosed in the Reiland '667 patent. A cylindrical shaft 176 has an overall length of approximately 9 inch while drive section 174 has a length of approximately 0.320 inch and leading section 172 has a length of 0.08 inch.

The drive section 172 has a maximum outer diameter of 0.107 inch, section 174 has a maximum outer diameter of 0.138 inch, and the shaft 176 has an outer diameter of 0.187 inch. Use of the hexagonal section 172 enables the body 142 to have a greater wall thickness in this area while the drive section 174 allows greater torque to be applied to the body 142 in its thicker region.

A central passageway 178 accommodates a guidewire so that, after a guidewire is placed within a bone tunnel between a wall of the tunnel and an object such as a bone plug to be secured within the tunnel, the interference implant 140, after being secured to a driver 170, is advanced together over the guidewire and into the tunnel. The interference implant is linearly inserted partially into the bone tunnel between the object and the wall of the tunnel until a portion of the helical thread lies in the tunnel. Torque is subsequently applied to the driver to rotate the interference implant spirally about its longitudinal axis, which causes the implant to screw deeper into the bone tunnel to secure the object within the tunnel.

Prior to inserting an interference implant into the tunnel, a tap 180, FIG. 9A, is utilized in some situations. The tap 180 includes a distal tap body 182, a shaft 184, and a proximal handle 186. A central longitudinal passage 188 extends therethrough for accommodating a guidewire.

The tap body 182 is shown in greater detail in FIG. 9B having a configuration similar to that of the interference implant to be subsequently inserted along a path formed by the tap. A smooth conical region 185 merges with a helical thread 187 along the proximal remainder of the tap body 182. A proximal socket 189 accommodates a narrowed tip of shaft 184. In one construction, shaft 184 has an outer diameter of 0.187 inch, an inner diameter of 0.67 inch, and the narrowed leading section has a length of 0.110 inch and an outer diameter of 0.100 inch.

The tap 180 is especially desired when the interference implant is made of a softer bioabsorbable material. Lower insertion torque is required to drive the interference implant into the tunnel when it is placed along a pre-established path made by the tap 180.

The body of the interference implant according to the present invention can be formed of a non-absorbable polymer such as Delrin polyacetal available from DuPont or of a bioabsorbable material such as polylactic acid (lactide), polyglycolic acid (glycolide) disclosed in U.S. Pat. No. 3,739,773 (Schmitt et al.), or copolymers disclosed in U.S. Pat. Nos. 4,300,565 (Rosensaft et al.) and 4,429,080 (Casey et al.), all of which are incorporated herein by reference. A combination of absorbable and non-absorbable materials to form a partially absorbable implant can also be utilized.

Figure 5:
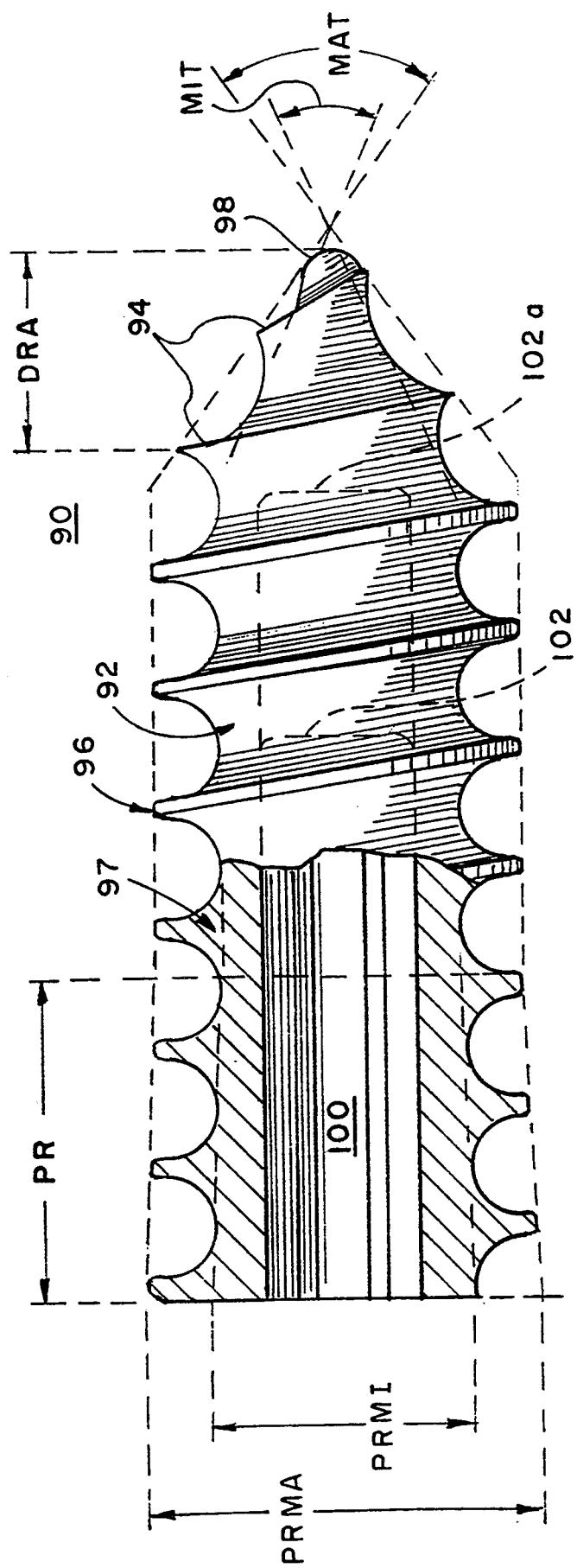
FIG. 5 is a side, partial cross-sectional view of a novel 9 mm interference screw which is coated with a different material.

An absorbable coating 92, FIG. 5, or coating 192, FIG. 7, preferably is a substance exhibiting a low coefficient of friction such as polycaprolate. An acceptable polycaprolate copolymer is a random copolymer of 85 weight percent epsilon-caprolactone and 15 weight percent glycolide. Other suitable coatings are disclosed in U.S. Pat. No. 4,788,969 (Jarrett et al.), which is incorporated herein by reference. In addition to reducing insertion torque, the absorbable coating can contain a pharmaceutical, a growth factor, or other compound. Additionally, the coating can have a selected absorption property to disappear within a desired period to enhance bone ingrowth and attachment to the screw.

As a coating over an absorbable screw body, the absorbable coating can serve as a barrier to body fluids to affect the rate of absorption of the main screw body. An absorbable coating according to the invention has a different composition than the screw body to provide one or more different selected properties such as a different coefficient of friction or rate of absorption.

Although specific features of the invention are shown in some drawings and not in others, this is for convenience only as each feature may be combined with any or all of the other features in accordance with the invention.

Other embodiments will occur to those skilled in the art and are within the following claims.

What is claimed is:

1. A surgical interference implant comprising:
   an elongated body formed of a biocompatible material, having a distal end and a proximal end, and having a longitudinal axis extending between said distal and proximal ends;
   said proximal end defining means for engaging a driver and lacking an enlarged head member;
   said body defining a conical region having a smooth outer surface and extending proximally from said distal end along a first, distal portion of said body to enable initial linear insertion of said body into a bone tunnel between a wall of the bone tunnel and an object to be secured therein;
   a helical thread disposed about a second, proximal portion of said body to enable subsequent rotational insertion of said body deeper into the bone tunnel, said proximal portion extending from said conical region to said proximal end, and said body having a body major diameter and a body minor diameter in said second, proximal portion; and
   said first, distal portion being inclined at a first angle relative to said longitudinal axis, and said body major diameter and said body minor diameter of said second, proximal portion each being inclined at a second, more acute angle along a substantial length of said proximal portion.

2. The implant of claim 1 wherein said helical thread extends from a proximal edge of said smooth outer surface to said proximal end of said body.

3. The implant of claim 1 wherein said body defines a passageway extending between said distal and proximal ends to accommodate a guidewire.

4. The implant of claim 1 wherein said biocompatible material is a bioabsorbable material.

5. The implant of claim 1 wherein said means for engaging a driver includes a polygonal drive socket formed in said proximal end.

6. The implant of claim 1 wherein said first angle is between ten to twenty degrees and said second angle is between one to ten degrees.

7. A surgical interference implant comprising:
an elongated body formed of a biocompatible material, having a longitudinal axis, and having a distal end and a proximal end;
said proximal end defining means for engaging a driver and lacking an enlarged head member;
said body defining a conical region having a smooth outer surface and extending proximally from said distal end along a first, distal portion of said body to enable initial linear insertion of said body into a bone tunnel;
a helical thread disposed about a second, proximal portion of said body to enable subsequent rotational insertion of said body deeper into the bone tunnel, said helical thread extending from a proximal edge of said smooth outer surface to said proximal end of said body, and said body having a body major diameter and a body minor diameter in said second, proximal portion; and
said first, distal portion being inclined at a first angle relative to said longitudinal axis, and at least one of said body major diameter and body minor diameter of said second, proximal portion being inclined at a second, more acute angle.

8. The implant of claim 7 wherein said means for engaging a driver includes a polygonal drive socket formed in said proximal end.

9. The implant of claim 8 wherein said body defines a passageway extending between said distal and proximal ends to accommodate a guidewire.

10. The implant of claim 8 wherein said biocompatible material is a bioabsorbable material.

11. The implant of claim 8 wherein said first angle is between ten to twenty degrees and said second angle is between one to ten degrees.

12. A method of securing an object within a bone tunnel, comprising:
forming a tunnel in a bone;
inserting an object into the bone tunnel;
providing an interference implant including:
an elongated body formed of a biocompatible material, having a longitudinal axis, and having a distal end and a proximal end;
the proximal end defining an element for engaging a driver and lacking an enlarged head member;
the body defining a conical region having a smooth outer surface and extending proximally from the distal end along a first, distal portion of the body;
a helical thread disposed about a second, proximal portion of the body, and the body having a body major diameter and a body minor diameter in the second, proximal portion; and
said first, distal portion being inclined at a first angle relative to the longitudinal axis, and at least one of the body major diameter and body minor diameter of the second, proximal portion being inclined at a second, more acute angle along a substantial length of said proximal portion;
selecting an appropriately sized driver and connecting the driver with the element for engaging;
linearly inserting the interference implant partially into the bone tunnel between the object and a wall of the tunnel until a portion of the helical thread lies within the tunnel; and
subsequently applying torque to the driver to rotate the interference implant spirally about its longitudinal axis and cause the implant to screw deeper into the bone tunnel to secure the object within the tunnel.

13. The method of claim 12 wherein the object is a bone plug of a replacement ligament.

14. The method of claim 13 wherein the tunnel is formed in a femur at a knee joint.

15. The method of claim 14 wherein the helical thread extends from a proximal edge of the smooth outer surface to the proximal end of the body.

16. The method of claim 15 wherein the body defines a passageway extending between the distal and proximal ends to accommodate a guidewire.

17. The method of claim 15 wherein the biocompatible material is a bioabsorbable material.

18. The method of claim 15 wherein the means for engaging a driver includes a polygonal drive socket formed in the proximal end.

19. The method of claim 15 wherein said first angle is between ten to twenty degrees and said second angle is between one to ten degrees.

* * * * *